United States Patent

Pardinas

Patent Number: 5,232,669
Date of Patent: Aug. 3, 1993

[54] PIPETTE TIP WITH SELF-ALIGNING AND SELF-SEALING FEATURES

[75] Inventor: Guillermo P. Pardinas, Miami, Fla.

[73] Assignee: Abbott Laboratories, Abbott Park, Ill.

[21] Appl. No.: 790,380

[22] Filed: Nov. 8, 1991

[51] Int. Cl.⁵ .............................................. B01L 3/02
[52] U.S. Cl. .................................. 422/100; 422/99; 422/104; 206/562; 206/563; 73/864.01; 73/864.14
[58] Field of Search .................... 422/99, 100, 104; 206/562, 563; 73/863.32, 864.01, 864.14, 864.21

[56] References Cited

U.S. PATENT DOCUMENTS

| | | | |
|---|---|---|---|
| 3,853,217 | 12/1974 | Scordato et al. | 206/562 X |
| 4,072,330 | 2/1978 | Brysch | 73/864.14 |
| 4,130,978 | 12/1978 | Cohen | 206/562 X |
| 4,298,570 | 11/1981 | Lillig et al. | 422/100 X |
| 4,707,337 | 11/1987 | Jeffs et al. | 422/100 |
| 4,748,859 | 6/1988 | Magnussen, Jr. et al. | 73/864.01 |
| 4,824,641 | 4/1989 | Williams | 422/100 |
| 4,863,695 | 9/1989 | Fullemann | 422/100 |
| 4,961,350 | 10/1990 | Tennstedt | 73/864.14 X |
| 5,057,282 | 10/1991 | Linder | 422/104 |

Primary Examiner—James C. Housel
Assistant Examiner—Maureen M. Wallenhorst
Attorney, Agent, or Firm—Frank S. Ungemach

[57] ABSTRACT

A pipette tip for use in automated assay testing systems includes an annular, protruding seal ring on the interior wall of the pipette for engaging a sealing surface on a probe to provide a resilient seal. The pipette tip also includes a positive stop for assuring proper positioning and alignment of the pipette tip on the probe for facilitating mounting of the pipette tip on the probe while minimizing variation in the loading and unloading forces required. Locator surfaces are provided on the exterior of the pipette tip for precisely aligning the pipette tip in the system rack for positioning the pipette tip relative to the probe.

16 Claims, 3 Drawing Sheets

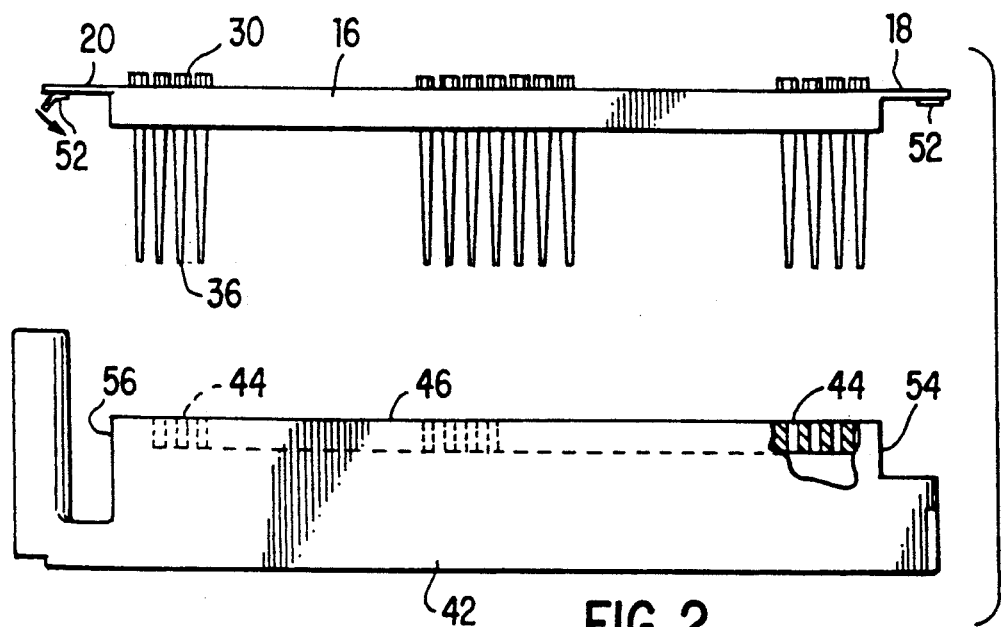
FIG. 2
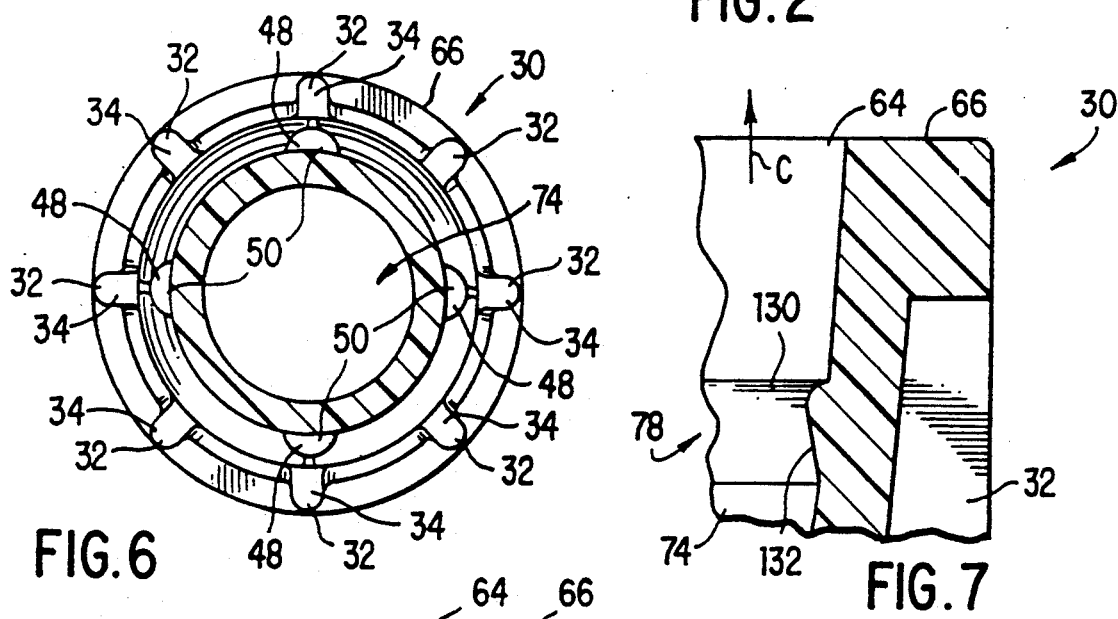
FIG. 6
FIG. 7
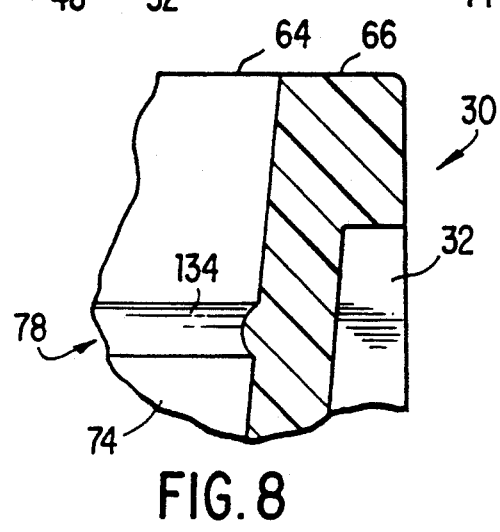
FIG. 8

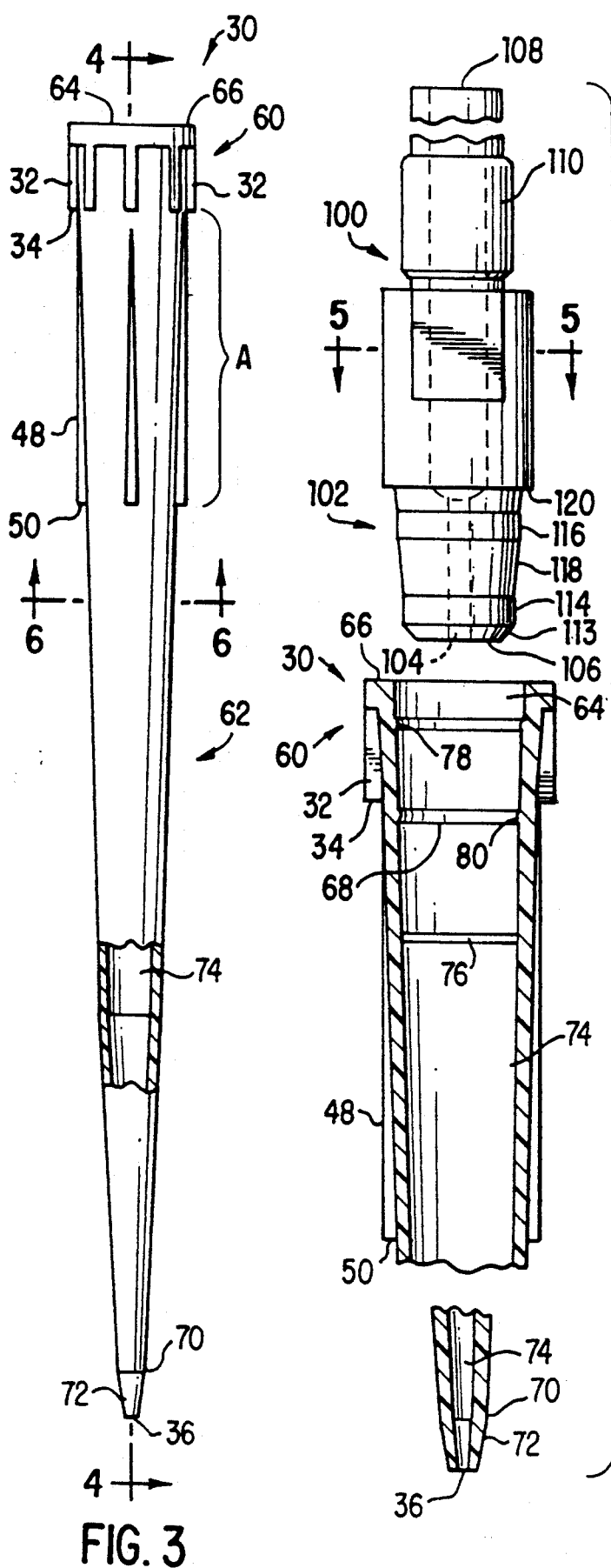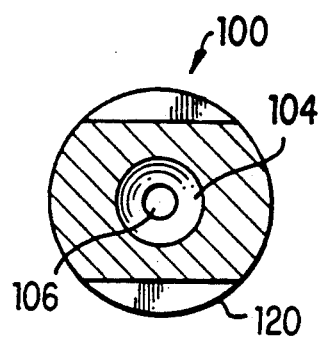
FIG. 3
FIG. 4
FIG. 5

PIPETTE TIP WITH SELF-ALIGNING AND SELF-SEALING FEATURES

BACKGROUND OF THE INVENTION

The invention is generally related to a pipette tip for aspirating and dispensing test samples and reagents and is specifically directed to a pipette tip having integrated alignment and sealing features.

DESCRIPTION OF THE PRIOR ART

It is known to utilize pipette tips in an automated reagent analysis system wherein a plurality of pipettes are positioned in a pipette rack or carrier located on the system and an automated probe is mounted on the end of a robot arm, wherein the probe is positioned over one of the pipettes in the carrier and inserted in the pipette for engaging the pipette. In the prior art, the pipette included a tapered inner passageway, and insertion of a cylindrical probe into the pipette generated a wedge fit, whereby the pipette was mounted on the prove and a seal was effected between the probe peripheral cylindrical surface and the tapered annular inner wall of the pipette. The robot arm then lifted the probe and pipette and performed a series of movements and operations for aspirating and dispensing both patient samples and the reagents. Upon completion of the operations, the robot arm moved the probe, and pipette to a disposal station, where an automated mechanism engaged the pipette and held it as the probe was withdrawn, for removing the pipette from the probe. The probe was then free to repeat the cycle with a new pipette.

The pipette tips of the prior art did not permit precise sealing and alignment of the pipette with the probe due to the reliance on the taper of the passageway in the pipette. This construction required the probe to seek a proper wedge and sealing relationship with each individual pipette. While this was effective for most operations, the loading force for loading the pipette onto the probe could vary by as much as +/−5 pounds. In addition, because of the wedge type locking mechanism utilized for locking the probe onto the pipette, the removal or unloading forces for removing the pipette from the probe also could vary by as much as +/−5 pounds.

This problem was further magnified because it was required to sufficiently force the probe into the tapered pipette to effect a seal by force and deformation of the tapered annular inner wall of the pipette.

In addition, the pipette tips of the prior art had to be hand-loaded in the rack, one at a time. This was a time consuming process and required physical handling of the pipettes by personnel.

SUMMARY OF THE INVENTION

The subject invention is directed to a pipette tip overcoming the disadvantages of the prior art. Specifically, the pipette tip of the invention includes integral alignment and sealing features permitting a probe to be inserted in the pipette with precision and with a minimum of force while effecting a redundant seal and positively positioning the pipette in a repeatable manner on the probe for performing the various fluid aspiratory and dispensing operations. In addition, the pipette tip of the subject invention includes locator surfaces on the exterior of the pipette for accurately positioning the pipette tip in the rack, assuring that the probe and pipette are in a calibrated, controlled relationship relative to one another, greatly enhancing the capability of the probe to engage the pipette and form a seal therewith.

In the preferred embodiment of the subject invention, the pipette tip and probe combination has reduced the loading and unloading force variance to less than +/−1 pound. In addition, a positive, resilient, redundant seal is provided, greatly enhancing the sealing capability of the pipette while reducing the forces required to engage the seal.

It is another feature of the invention that a plurality of the pipettes are adapted to be positioned in a container which is adapted to be placed directly over the rack or carrier in the system for properly positioning and loading the pipettes into the carrier. A plurality of locator surfaces are provided on the pipettes, the first of which properly maintain the pipettes in the container and the second of which engage a calibrated locator surface on the carrier as the pipettes are simultaneously inserted therein via the container. The container is adapted to be temporarily adhesively secured to the carrier for maintaining proper position of the pipettes during the operation.

The outer tip of each pipette is designed to reduce the meniscus formed when aspirating and dispensing samples, reducing the amount of waste and reducing the exposure of the samples and reagents to outside elements.

The probe includes a flat or cylindrical sealing surface which is adapted to engage an annular seal in the base of the pipette, providing a sliding, positive, resilient seal for sealing the coupling between the pipette and the probe. The outer end of the pipette includes a stop surface which is adapted to be engaged on a positive stop provided on the probe, assuring that the probe is aligned with and inserted into each pipette in a repeatable, controlled manner.

In the preferred embodiment, the seal is defined by a plurality of axially spaced, concentric annular rings mounted in and projecting inwardly from the inside wall of the pipette for engaging sealing surfaces on the probe as the probe is inserted in the pipette. The concentric seals also assist in properly aligning the probe and the pipette. The plurality of rings provide a positive, resilient, redundant seal, greatly improving the seal between the pipette and the probe over prior art pipette tips.

The base of the pipette includes ribs which both serve as locator surfaces for properly positioning the pipette tip in the carrier and strengthen the pipette tip to reduce deformation as the probe is inserted into the tip. The pipette tip of the subject invention has a volume repeatability for aspirating and dispensing fluids within a 30 microliter control range for a 1.09 milliliter pipette tip.

It is, therefore, an object and feature of the subject invention to provide a pipette tip having positive locator surfaces for controlling the movement of a probe into the pipette tip as the probe engages the pipette tip.

It is a further object and feature of the subject invention to provide a pipette tip having an integral sealing mechanism adapted to engage a sealing surface on the probe as the probe enters the pipette.

It is another object and feature of the subject invention to provide a resilient, redundant seal for increasing the seal between the probe and the pipette tip.

It is yet another object and feature of the subject invention to provide a pipette tip and probe combination wherein the loading and unloading forces for mounting the pipette on the probe and removing the pipette from the probe are consistent and predictable.

It is also an object and feature of the subject invention to provide for means for simultaneously loading a plurality of pipette tips in the system carrier.

Other objects and features of the invention will be readily apparent from the accompanying drawings and detailed description of the preferred embodiment.

BRIEF DESCRIPTION OF THE DRAWINGS

FIG. 2 is an exploded front view illustrating a carrier in combination with the pipette and container system of FIG. 1.

FIG. 3 is an enlarged front view of a pipette in accordance with the subject invention.

FIG. 4 is a section view taken generally along the line 4—4 of FIG. 3 and includes a probe for receiving the pipette.

FIG. 5 is a section view taken generally along the line 5—5 of FIG. 4.

FIG. 6 is a section view taken generally along the line 6—6 of FIG. 3.

FIG. 7 is an enlarged fragmentary view looking in the same direction as FIG. 3 and showing the detail of the sealing surface.

FIG. 8 is a view similar to FIG. 7, showing an alternative embodiment of the sealing surface.

DETAILED DESCRIPTION OF THE PREFERRED EMBODIMENT

Figure 1:
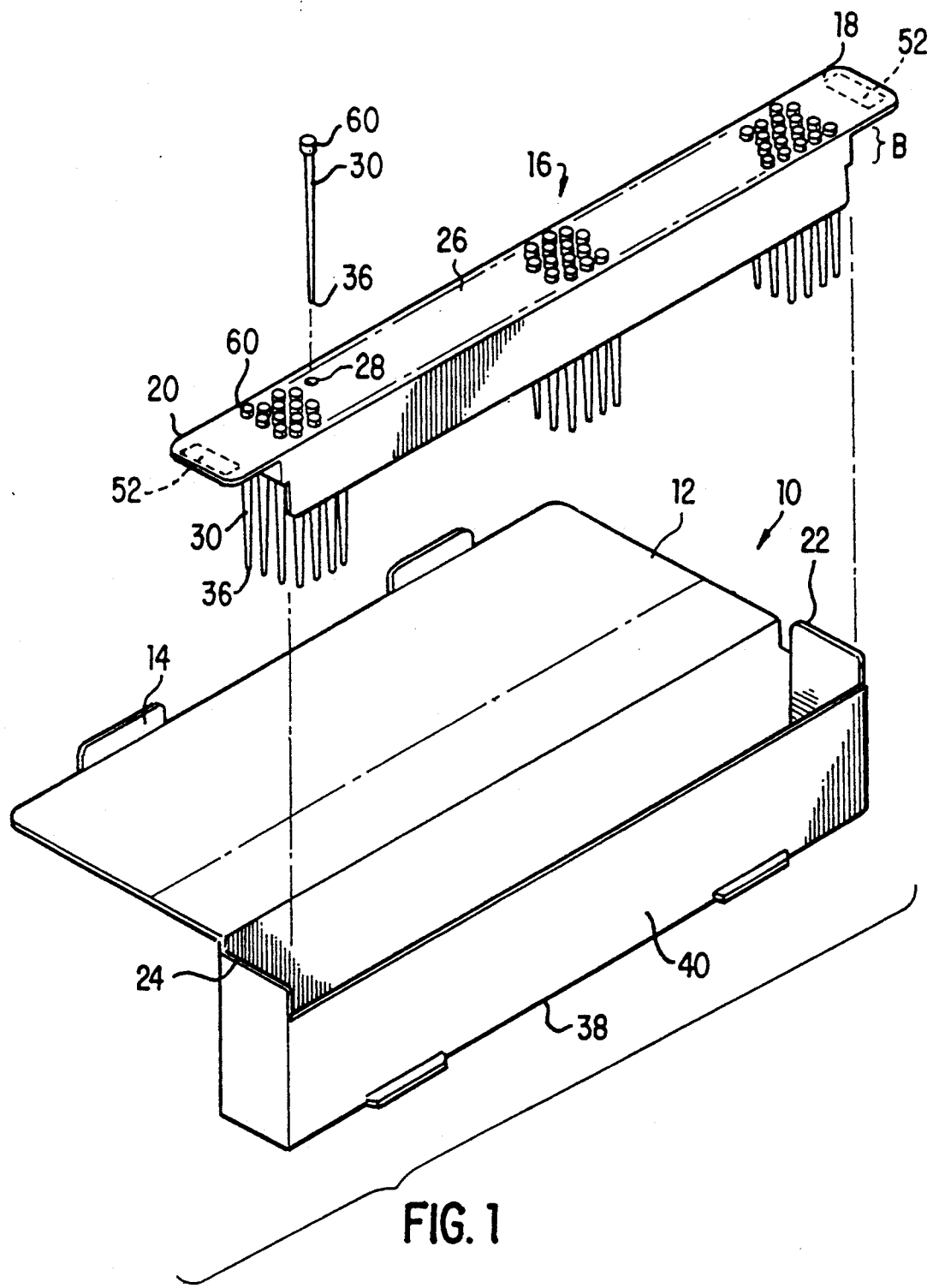
FIG. 1 is an exploded perspective view of a container, box and pipette tips in accordance with the subject invention.

A pipette container and pipettes made in accordance with the subject invention are shown in FIG. 1. In the preferred embodiment, the container comprises a box 10 having a closed bottom, upstanding side walls and a hinged top 12 with a flap 14. A tray 16 is adapted to be received in the open top of the box 10 and has a pair of outwardly extending tabs 18 and 20 which are adapted to be positioned on the upper edges 22 and 24 of the box when the tray is inserted in the box. The tray 16 includes an upper, generally horizontal surface 26 having a plurality of holes or through apertures 28 each adapted for receiving a pipette tip 30. As better shown in FIG. 3, the pipette tip 30 includes a plurality of longitudinally extending ribs 32 around its outer end, each having a bottom edge 34 which is adapted to engage the top surface 26 of the tray 16 for positioning and holding the pipette in the tray. When the pipettes are loaded in the apertures 28, they depend from the tray, as shown in FIG. 1. The tray is then placed in the box 10 with the tabs 18 and 20 extending outwardly from the edges 22 and 24, respectively. The locator end 34 of each of the ribs 32 maintains the pipette in the tray such that the bottom end 36 of the pipette is above the closed bottom 38 of the box. The lid 18 may then be closed over the tray, with a flap 14 secured to the front wall 40 of the box. Tabs 18 and 20 project outwardly from the box when the lid 12 is in the closed position.

As shown in FIG. 2, the pipette tray 16 and pipettes 30 are adapted to be removed from the box 10 with the pipettes positioned in the tray. The user may grasp the tabs 18 and 20 for removing the pipettes and tray from the box and for positioning the pipettes relative to the pipette rack or carrier 42 of the analyzer system. The pipette carrier 42 includes a plurality of pipette receptacles 44, each for receiving and positioning a pipette in the analyzer system. The top surface 46 of the carrier 42 is a precision calibrated surface, providing a precise positioning relationship between the surface 46 and a probe at the end of a robot arm (not shown) for positioning the probe relative to the pipette carrier in the manner well known to those who are skilled in the art.

The user positions the pipettes 30 in the tray 16 over the receptacles 44 in the carrier 42, as shown in FIG. 2. The tray 16 is then lowered onto the carrier 42. The pipettes 30 are received in the respective receptacles 44. As better shown in FIG. 3, a plurality of elongate ribs 48 are provided on the exterior wall of the pipette 30 and radially inwardly of the ribs 32. Each of the ribs 48 have a lower end 50 which is adapted to engage the locator surface 46 on the carrier 42, for properly positioning the pipette relative to the carrier. The distance "A" from the outer end of the pipette 30 to the lower end of the ribs 48 is greater than the thickness "B" of the tray 16, whereby as the pipettes 30 are lowered into the carrier 42, the locator surface 46 engages the rib ends 50 and the tray 16 drops down to the carrier and out of interfering relationship with the pipettes, assuring that the pipettes are properly positioned in the carrier.

In the preferred embodiment of the invention, each of the tabs 18 and 20 includes an adhesive such as tape 52 or the like, as shown in FIG. 2. Where desirable, the tape 52 may be provided with a peelable protective layer to assure that the tape does not become contaminated or prematurely engaged during shipping when the tabs 18 and 20 are exposed outwardly of the box 10. After the pipettes are properly positioned in the carrier 42 and the tray 16 is lowered onto the locator surface 46, the tabs 18 and 20 may be folded down against the outer end walls 54 and 56, respectively of the carrier 42. The tape strips 52 are then pressed against the walls 54 and 56 for holding the tray in position during operation of the analyzer system. After all of the pipettes have been removed from the carrier during operation, or after operations is completed, the tray 16 may be removed from the carrier 42 by removing the tabs 18 and 20 from the walls 54 and 56 and pulling the tray upwardly to the position of FIG. 2, from which it may be discarded.

An enlarged plan view of the pipette tip 30 is shown in FIG. 3. As there shown, the pipette tip 30 includes a base 60, a pipette body 62, a lower open end 36 and an upper open end 64. A shoulder or outer rim 66 is positioned at the upper open end 64 at the outer end of the base 60. The shoulder 66 provides a locator surface for providing a positive stop for mounting the pipette 30 on a probe. A plurality of ribs 32 depend downwardly from the shoulder 66 and have a lower end 34 which defines a stop surface for positioning the pipette tips 30 in the tray 16. The ribs also reinforce the pipette base to minimize deformation in the sealing as the probe is inserted in the pipette. A plurality of longer ribs 48, disposed radially inwardly of the ribs 32 and adapted to be in noninterfering relationship with the apertures 28 in the tray 16 extend downwardly along the tapered body 62 of the pipette tip and terminate in a precisely positioned end 50 defining a locator surface for positively and accurately positioning the pipette tips 30 in the carrier 42 when the pipettes are received in the individual receptacles 44. The body 62 is of a continuous taper from the bottom 68 of the base 60 to a transition point 70 near the lower end 36. It will be noted that the taper is increased in the transition section 72 between the transition point 70 and the lower end 36. It has been found that the increased taper in the transition section 72 substantially reduces the meniscus formed at the lower end 36 during use of the pipette, reducing the inaccuracy in metering and reducing exposure of fluids to outside elements.

The interior passageway of the pipette is more clearly shown in FIG. 4. As there shown, the interior pipette passageway 74 is of a continuous taper from the lower pipette tip end 36 to the open upper base end 64. In the preferred embodiment, the pipette passageway 74 is positioned on the center axis of the pipette and has a continuous taper of 2.180 for a pipette having a diametric opening at lower end 36 of 0.031 inches and an overall length of 3.35 inches. The diametric opening at upper base end 64 is 0.286 inches.

In the preferred embodiment, the pipette tip 30 is made of a high density polyethylene and is translucent white in color. The pipette is designed to be molded in a single stop process. More importantly, red blood cells do not cling to high density polyethylene assuring a complete purging of the red blood cells from the pipette when dispensed. The high density polyethylene is impervious to blood, reducing staining and increasing visibility of the contents of the pipette during the testing operation. A fill line 76 is provided on the interior wall of the passageway 74 and is visible through the pipette wall. In typical operation, the pipette is never filled above the fill line 76.

The base 60 includes a first annular ring 78 extending around the interior wall of the passageway 74 and protruding inwardly therefrom to define a resilient sealing surface. In the preferred embodiment, a second, concentric annular ring 80 is provided in spaced relationship with the annular ring 78 for providing a second, redundant, resilient sealing surface.

As is also shown in FIG. 4, the probe 100 is adapted to be inserted in the open base end 64 of the pipette 30 and into the tapered passageway 74. The plug end 102 of the probe is adapted to be received in the passageway 74 in a noninterfering relationship. The probe includes a central through channel 104 having open outer ends at 106 and 108. A mounting surface 110 is provided on the probe, and in the preferred embodiment is designed to be mounted in and engaged by a robot arm (not shown) in a press fit relationship with a socket provided in the robot arm. Other means for mounting the probe on the robot arm could be incorporated, as well understood by those skilled in the art.

The robot arm is then connected to a vacuum system (also not shown), for drawing a vacuum on the probe. The probe plug tip 102 includes a tapered front surface 113 that extends from the end 106 of the probe plug tip 102 to a first cylindrical flat 114, a first cylindrical flat 114 and a second concentric cylindrical flat 116 with a tapered transition surface 118 therebetween. The tapered front surface 113 preferably has a draft that permits smooth coupling of the probe plug tip 102 and the pipette 30. In the preferred embodiment, the probe tip 102 is adapted to be inserted into the open end 64 of the base 60 of the pipette and the flat cylindrical sealing surfaces 114 and 116 on the probe tip are adapted to be received in sliding engagement by the annular rings 78 and 80 on the pipette tip 30, respectively. The annular rings 78 and 80 are dimensioned such that they form a resilient sealing engagement with the cylindrical flats 114 and 116, whereby a resilient redundant seal is provided between the pipette tip and the probe tip. A shoulder 120 is provided at the base of the probe tip 102 for engaging the rim or shoulder 66 on the base 60 of the pipette tip for providing a positive stop for limiting movement of the probe tip into the pipette tip. The annular probe shoulder 120, pipette shoulder 66, concentric annular seals 78 and 80 and probe sealing surfaces 114 and 116 work in combination to assure proper axial alignment of the probe with the pipette tip.

As shown in FIG. 7, the annular sealing ring 78 is of a rounded upper surface or edge 130 tapering into a cylindrical section 132. This is to assure easy removal of the molded probe from the mold cavity when withdrawn axially in the direction of arrow C. However, it will be readily understood that any annular sealing surface could be utilized such as the arcuate surface 134 shown in FIG. 8. A channel could be provided in the interior surface of the pipette and an independent O-ring inserted, if desired. However, the integral sealing surfaces of the preferred embodiment reduce manufacturing costs while assuring a resilient redundant seal between the probe tip and the pipette tip.

While certain features and embodiments of the invention have been described in detail herein, it will be readily understood that the invention encompasses all enhancements and modifications within the scope and spirit of the following claims.

I claim:

1. An assembly including a pipette adapted to be mounted on a probe for aspirating and dispensing a calibrated volume of fluid, comprising:
   a. a tray having a top surface, a predetermined depth and a plurality of apertures for positioning and holding said pipette in said tray;
   b. a carrier having a locator surface and a plurality of apertures for positioning and holding a pipette in said carrier; and
   c. a pipette having
      i. an elongated body having a longitudinal axis, a central through passageway and open opposite ends, one of said ends defining a pipette tip;
      ii. a base on the end of the body opposite the pipette tip, the base comprising an outer shoulder, which engages the top surface of the tray, and an internal, through bore in communication with the central through passageway; and
      iii. a plurality of body ribs on the exterior wall of the body located radially inwardly of the outer shoulder of the base, wherein each body rib has an end at a distance from the base greater than the predetermined depth of the tray which engages the locator surface of the carrier such that when the tray and carrier are engaged, the body rib ends engage the locator surface and the base disengages from the top surface of the tray.

2. The pipette of claim 1, wherein the pipette further comprises a sealing member on the internal surface of the bore which is adapted for engaging and forming a sealed connection with a sealing surface of the probe when the sealing surface is received in said bore.

3. The pipette of claim 2, wherein said sealing member comprises a first resilient annular ring.

4. The pipette of claim 3, wherein the sealing member further comprises a second resilient annular ring on the internal surface of the bore which is concentric with the first annular ring, said second annular ring adapted for engaging and forming a sealed connection with the sealing surface of the probe when the sealing surface is received in said bore.

5. The pipette of claim 2, wherein said pipette base is adapted for positively engaging a mounting surface of said probe, wherein said mounting surface is adapted for positively engaging the outer shoulder of said pipette base when the sealing surface of the probe is received in said bore for defining a positive stop for limiting the relative movement between the pipette and the probe.

6. The pipette of claim 1, wherein the tray further includes opposite outer ends and a hinged tab secured to each of said opposite ends, the hinged tabs adapted to be moved from a free position to a carrier engaging position.

7. The pipette of claim 1, wherein said outer shoulder further comprises a plurality of longitudinally extending shoulder ribs disposed radially about and projecting radially outwardly from the periphery of the base, such that the shoulder ribs project out further from the base than the body ribs and the shoulder ribs extend from the shoulder of the base to an end point on the body of the pipette above the carrier engaging ends of the body ribs.

8. The pipette of claim 2, wherein the body, base and sealing member are of unitary molded construction.

9. The pipette of claim 8, wherein the unitary molded pipette is constructed of a high density polyethylene material.

10. The pipette of claim 1, wherein the pipette body comprises a first portion and a second portion each of predetermined length forming a continuous taper converging toward the pipette tip wherein the first portion which is adjacent to said base is defined by a truncated cone of a first taper and the second portion which is attached to the end of the first portion opposite the base and adjacent to said pipette tip is defined by a truncated cone of a second taper.

11. The pipette of claim 2, wherein said central through passageway and said bore are of a continuous taper converging toward the pipette tip and wherein the sealing member comprises a first sealing element and a second, concentric sealing element at predetermined positions along the longitudinal axis of said tapered central passageway and said bore, and wherein said probe further comprises a tip adapted to be received in the central through passageway at the base end of the pipette, the tip having a generally tapered outer periphery and two sealing surfaces on the tapered outer periphery, such that a first sealing surface engages the first sealing element to form a sealed connection and a second sealing surface engages the second sealing element to form a sealed connection.

12. The pipette of claim 11, wherein said first and second sealing surfaces comprise concentric cylindrical sections disposed on said generally tapered periphery of said probe tip surface.

13. A pipette kit for carrying a plurality of pipettes which are adapted to be mounted on a carrier in an automated analyzer system the carrier having a locator surface disposed in a predetermined position relative to a probe and each of the pipettes adapted to be mounted on the probe for aspirating and dispensing a calibrated volume of fluid, the pipette kit comprising:

a tray comprising upper and lower surfaces for defining a tray thickness of a predetermined depth, a plurality of apertures extending through said tray thickness wherein each aperture is adapted for receiving and carrying a pipette, and the tray being adapted to engage the carrier such that each pipette inserts into a pipette receptacle in the carrier; and pipettes, each pipette comprising:
 a. an elongated body having a longitudinal axis, a central through passageway and open opposite ends, one of said ends defining a pipette tip;
 b. a base on the end of the body opposite the pipette tip, the base comprising an outer shoulder, which engages a top surface of said tray and an internal, through bore in communication with the central through passageway; and
 c. a plurality of body ribs on the exterior wall of the body located radially inwardly of the outer shoulder of the base, wherein each body rib has an end at a distance from the base greater than the depth of the tray and adapted to engage a locator surface of a carrier having a plurality of apertures for positioning and holding said pipette in said carrier, such that when the tray and carrier are engaged, the body rib ends engage the locator surface and the base disengages from the top surface of the tray.

14. The pipette kit of claim 13, wherein each pipette further comprises a sealing member on the internal surface of the bore which is adapted for engaging and forming a sealed connection with a sealing surface of the probe when the sealing surface is received in said bore.

15. The pipette kit of claim 13, wherein the tray further comprises opposite outer ends and a hinged tab secured to each of said opposite ends, the hinged tabs adapted to be moved from a free position to a carrier engaging position.

16. A pipette adapted to be mounted on a probe for aspirating and dispensing a calibrated volume of fluid, comprising:
 a. an elongated body having a longitudinal axis, a central through passageway and open opposite ends, one of said ends defining a pipette tip;
 b. a base on the end of the body opposite the pipette tip, the base comprising an internal, through bore in communication with the central through passageway, and an outer shoulder which is adapted to engage a top surface of a tray having a predetermined depth and a plurality of apertures for positioning and holding said pipette in said tray;
 c. a plurality of body ribs on the exterior wall of the body located radially inwardly of the outer shoulder of the base, wherein each body rib has an end at a distance from the base greater that the depth of the tray and adapted to engage a locator surface of a carrier having a plurality of apertures for positioning and holding said pipette in said carrier, such that when the tray and carrier are engaged, the body rib ends engage the locator surface and the base disengages from the top surface of the tray; and
 d. a plurality of longitudinally extending shoulder ribs disposed radially about and projecting radially outwardly from the periphery of the base, such that the shoulder ribs project out further from the base than the body ribs and the shoulder ribs extend from the shoulder of the base to an end point on the body of the pipette above the carrier engaging ends of the body ribs.

* * * * *

UNITED STATES PATENT AND TRADEMARK OFFICE
CERTIFICATE OF CORRECTION

PATENT NO. : 5,232,669
DATED : August 3, 1993
INVENTOR(S) : Guillermo P. Pardinas It is certified that error appears in the above-indentified patent and that said Letters Patent is hereby corrected as shown below:

Column 1, line 21, change "on the prove" to --on the probe--.

Column 1, line 40, change "as much as +/-S pounds" to --as much as ±5 pounds--.

Column 1, line 44, change "as much as +/-5 pounds" to --as much as ±5 pounds--.

Signed and Sealed this

Nineteenth Day of April, 1994

Attest:

BRUCE LEHMAN

*Attesting Officer*    *Commissioner of Patents and Trademarks*